Figure 1:
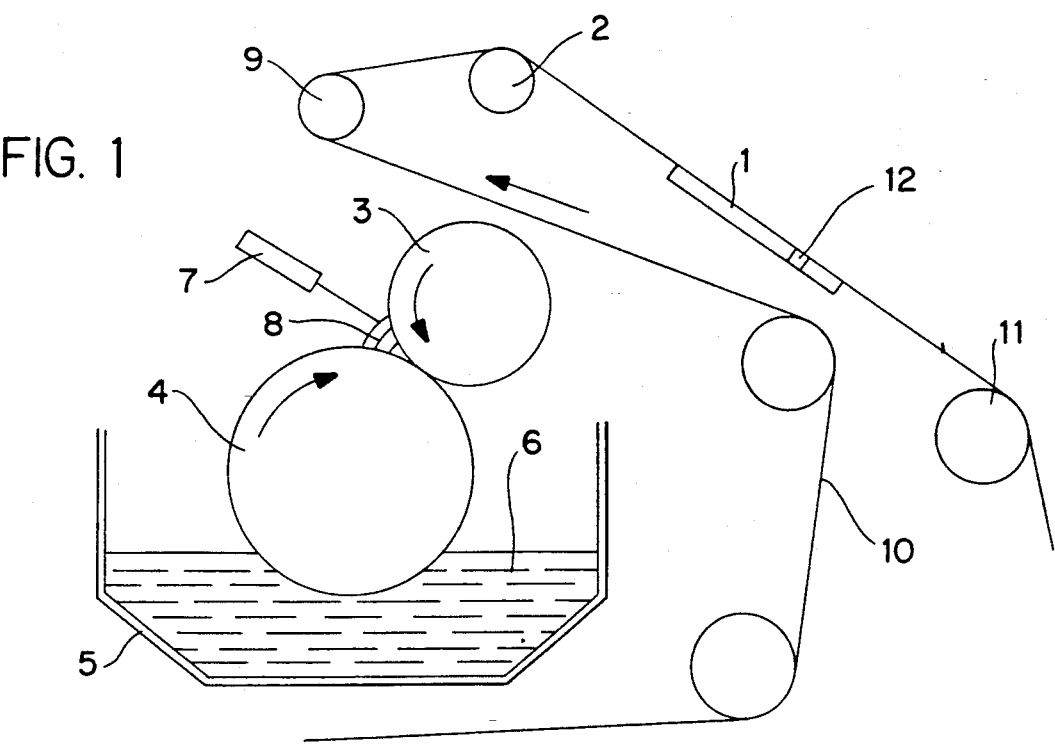

United States Patent [19]

Masurat et al.

[11] Patent Number: 5,170,128
[45] Date of Patent: Dec. 8, 1992

[54] DEVICE FOR DETECTING A SUFFICIENT GLUE COATING OF A PAPER STRIP

[75] Inventors: Heinz Masurat, Borstel-Hohenraden; Horst Gaisser, Hassloh; Meinhard Meyer, Appen-Unterglinde; Ingo Pautke, Hamburg, all of Fed. Rep. of Germany

[73] Assignee: B. A. T. Cigarettenfabriken GmbH, Hamburg, Fed. Rep. of Germany

[21] Appl. No.: 602,295

[22] PCT Filed: Mar. 3, 1990

[86] PCT No.: PCT/DE90/00152
  § 371 Date: Nov. 21, 1990
  § 102(e) Date: Nov. 21, 1990

[87] PCT Pub. No.: WO90/11518
  PCT Pub. Date: Oct. 4, 1990

[30] Foreign Application Priority Data

Mar. 25, 1989 [DE] Fed. Rep. of Germany ....... 3909990

[51] Int. Cl.⁵ .............................................. G01R 27/26
[52] U.S. Cl. ........................................ 324/664; 324/689
[58] Field of Search ............... 324/663, 664, 687, 689, 324/690; 131/905, 907, 908

[56] References Cited

U.S. PATENT DOCUMENTS

| | | | |
|---|---|---|---|
| 3,043,993 | 7/1962 | Maltby | 317/146 |
| 3,713,966 | 1/1973 | Lippke | 162/263 |
| 4,417,934 | 11/1983 | Vaughan | 131/905 X |

FOREIGN PATENT DOCUMENTS 3143526 6/1982 Fed. Rep. of Germany .

*Primary Examiner*—Jack B. Harvey
*Attorney, Agent, or Firm*—Roylance, Abrams, Berdo & Goodman

[57] ABSTRACT

A device, for detecting a sufficient glue coating on a first surface of a paper strip to be adhesively bonded in a cigarette machine, includes a sliding plate having a plate surface engaging a second surface of the paper strip, opposite to the first surface, and over which the paper strip runs in a first direction. A plurality of capacitive sensors, for detecting presence of moisture in the glue coating, on the first surface of the paper strip, are directed toward the second surface of the paper strip, are mounted in recesses in the sliding plate and are arranged in a row extending transversely to the first direction. A control is coupled to the sensors for evaluating signals emitted from the sensors and for emitting a fault signal for controlling the cigarette machine when the moisture sensed in the glue coating is insufficient.

18 Claims, 4 Drawing Sheets

DEVICE FOR DETECTING A SUFFICIENT GLUE COATING OF A PAPER STRIP

DESCRIPTION

The invention relates to a device for detecting a sufficient glue coating of a paper strip to be adhesively bonded in a cigarette machine.

To connect cigarette filters to the cigarette portion containing the tobacco, there is usually a filter cover paper which on the one hand wraps the filter and which on the other hand, by means of a projecting edge, connects the cigarette portion containing the tobacco to the filter. As a rule, the filter is joined together with the cigarette portion by gluing.

In cigarette machines in common use nowadays, as a rule the cigarettes are first produced as double cigarettes which are then cut open and drawn apart from one another. Double filters are then introduced into the interspace between the two cigarettes. The filters and the two lateral cigarette portions are then wrapped in the previously glue-coated filter cover paper, a lateral region of the filter cover paper in each case connecting the filter and cigarette to one another.

For particular reasons, filter cover papers used today are often equipped with zones of increased air permeability, in order to allow a ventilation of the filter region. It is therefore inadmissible to apply a glue layer onto the filter cover paper in this region.

It has been shown that it can happen, especially at high production speeds, that the glue coating applied to the filter cover paper has already dried before connection to the filter and the cigarette, to such an extent that there is no guarantee of a sufficient connection. It can happen, furthermore, that the glue-coating layer was applied too thinly and/or that its moisture content was too low. At all events, defective cigarettes are produced, and these can no longer be located during the further production process without additional action.

A process and a device for detecting the presence of a glue layer on a running web are known from EP 0,300,734 A2. Here, the increased light reflection of a glue layer in comparison with a reflection of the paper free of glue is evaluated and the presence of a glue coating thus established.

This process can detect only the presence, but not the thickness of a glue layer. Moreover, incorrect measurements as a result of a soiling of the optical components can occur.

German Offenlegungsschrift 3,143,526 makes known a process for monitoring a sufficient glue coating on a paper strip, in which the presence of a sufficient glue coating is detected by means of a capacitive sensor.

This device is not suitable for use on filter cover papers which have a glue coating in the form of a recurring pattern, since for this a highly accurate guidance of the paper strip in relation to the sensor is necessary and the sensor is incapable of distinguishing a recurring pattern from undesirable interruptions of the glue coating.

The object on which the invention is based is to provide a device for detecting a sufficient glue coating of a paper strip to be adhesively bonded, by means of which both the presence and the state of a glue coating applied especially in a recurring pattern can be detected shortly before the adhesive bonding of the paper strip in a cigarette machine.

This object is achieved by a device for detecting a sufficient glue coating on a first surface of a paper strip to be adhesively bonded in a cigarette machine, comprises a sliding plate having a plate surface engaging a second surface of the paper strip, opposite to the first surface, and over which the paper strip runs in a first direction. A plurality of capacitive sensors, for detecting presence of moisture in the glue coating, on the first surface of the paper strip, are directed toward the second surface of the paper strip, are mounted in recesses in the plate surface of the sliding plate and are arranged in a row extending transversely to the first direction. A control means is coupled to the sensors for evaluating signals emitted from the sensors and for emitting a fault signal for controlling the cigarette machine when the moisture sensed in the glue coating is insufficient.

By the use of the invention, it is possible to detect, immediately before a filter cover paper is connected to the filter and cigarette ends, whether the glue coating of the filter cover paper provided for this connection is sufficient or no longer allows a sufficient connection.

The moisture content of the glue coating is detected by capacitive sensors. If there is insufficient moisture as a result of excessive drying or because the glue layer is too thin, a fault signal is generated and separates the cigarettes glued in this way out of the further processing cycle.

The arrangement of the sensors underneath the filter cover paper guarantees that these always remain clean, without the possibility that, especially during a stoppage, the glue will adhere to the sensors. Preferably, the sensors are arranged directly in front of the cutting device for the filter cover paper, so that the state of the glue coating can be detected as near as possible to the location of the adhesive bonding.

The presence of a sliding plate ensures that the filter cover paper is guided exactly and therefore especially that a constant distance between the sensors and the filter cover paper is maintained. A possible swinging or fluttering of the filter cover paper can be reliably prevented by the provision of a curved sliding plate, groove-shaped channels in the sliding plate, suction connections in the sliding plate and/or a sharp run-on edge on the sliding plate.

Other features involve particular embodiments of the invention for use on a filter cover paper, on which the glue coating is applied in a recurring pattern.

The invention allows an exact metering of the glue coating and an improved fault detection, so that the rejection rate can be reduced and therefore the productivity increased.

Figure 2:
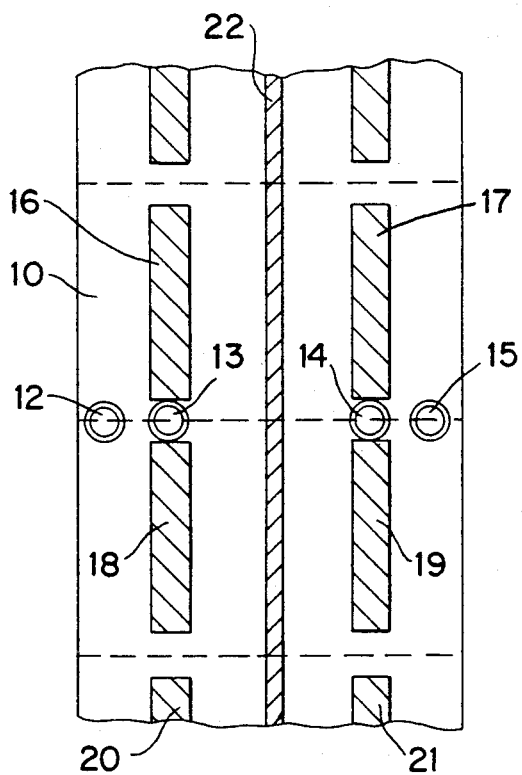
Figure 3:
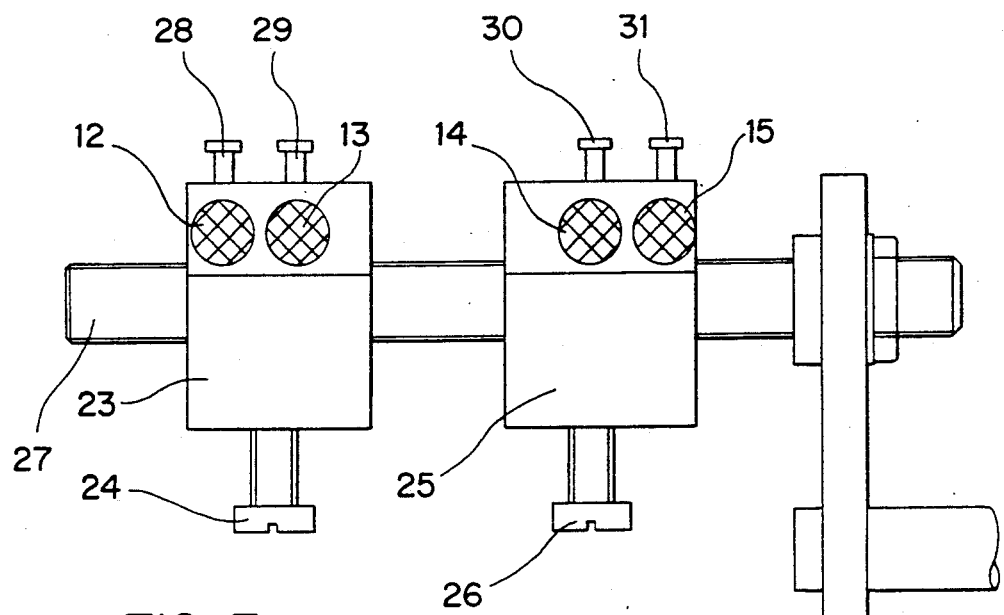
Figure 4:
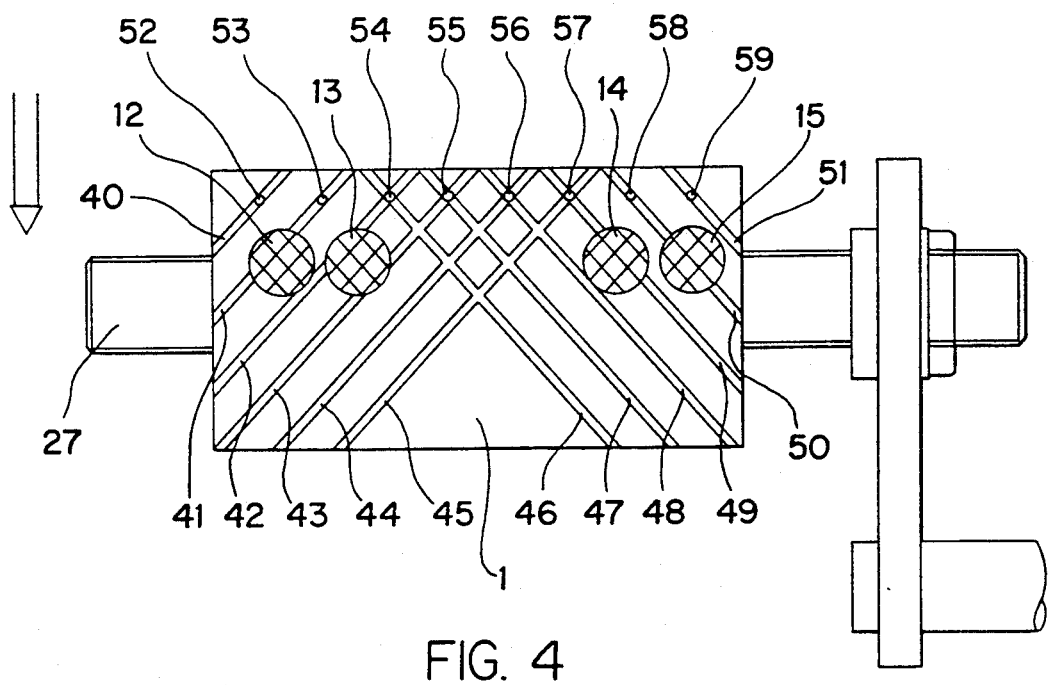
Figure 5:
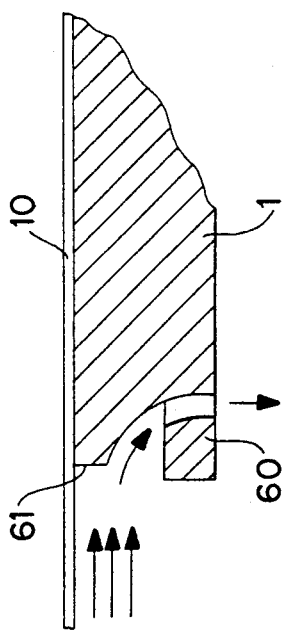
Figure 6:
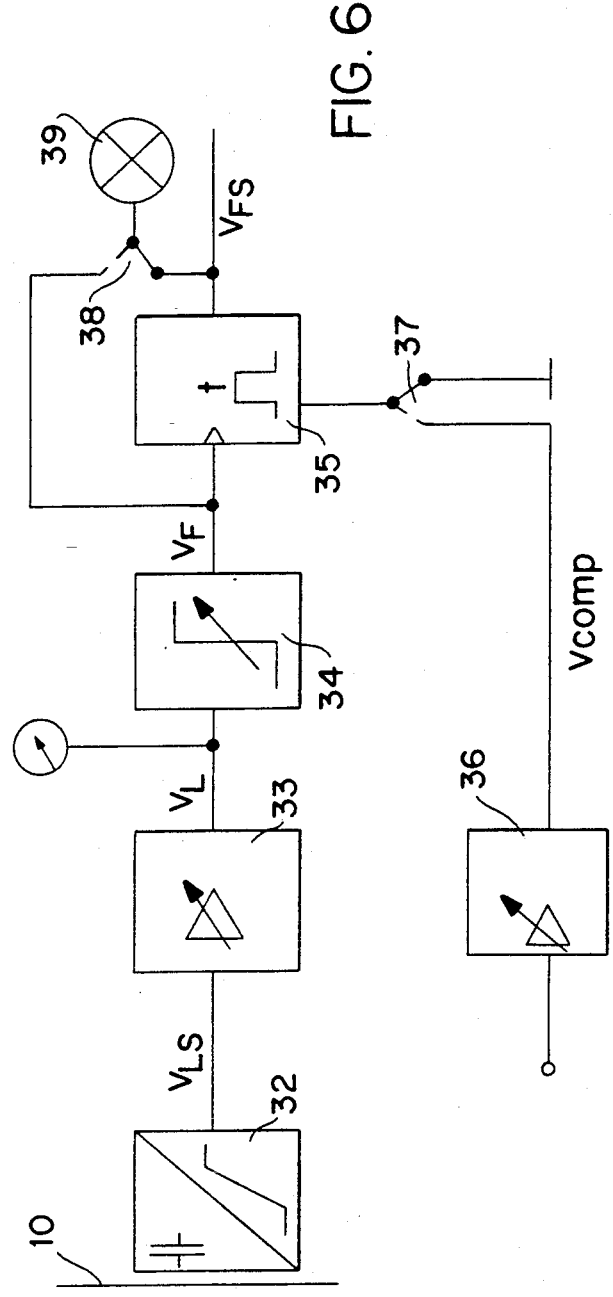
Figure 7:
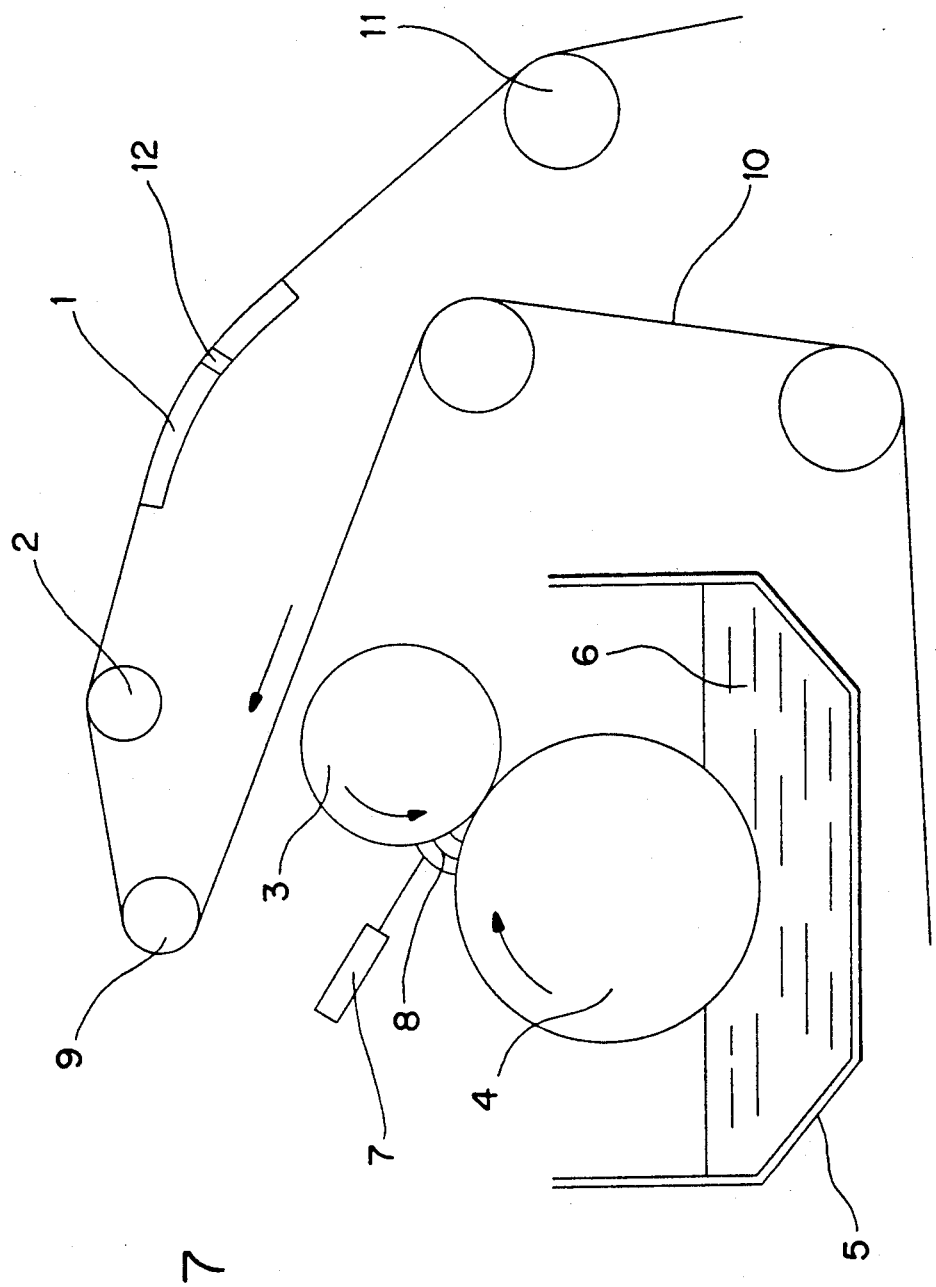

The invention is explained in more detail below by means of an exemplary embodiment. In the drawing FIG. 1 shows a diagrammatic side view of part of a cigarette machine in which the device according to the invention is arranged, FIG. 2 shows a top view of a filter cover paper with three-dimensionally associated sensors, FIG. 3 shows a view of mountings for sensors, FIG. 4 shows a top view of a mounting for sensors with additional air channels, FIG. 5 shows a side view of a sliding plate, FIG. 6 shows a block diagram of an evaluation circuit, and FIG. 7 shows a diagrammatic side view, similar to FIG. 1, but with a curved sliding plate.

FIG. 1 shows the glue-coating device on a cigarette machine. There is a glue pot 5 which is constantly filled with glue from a reservoir. Glue is received from this pot 5 via a rotating dipping roller 4 and is transferred onto a glue roller 3. The glue can be transferred from the glue roller 3 onto the filter cover paper 10 which can be pressed against the glue roller 3. The filter cover paper 10 runs as an endless strip over a plurality of deflecting rollers to a pivotable deflecting roller 9, by means of which the cover paper 10 can be pressed against the glue roller 3. After the glue coating has been transferred to the filter cover paper 10, the filter cover paper runs in the filter-attaching machine 10 to the connection point between the filter and cigarette and there wraps the filter and connects this to the cigarette.

The glue 6 received from the glue pot 5 by the dipping roller 4 forms, during the transfer to the glue roller 3, a glue bead 8 which can be detected via an infrared sensor. It can be ascertained at this point whether any glue at all has been received from the glue pot.

According to the invention, just in front of the point where the filters are attached to the cigarettes, a device for detecting a sufficient glue coating of the paper strip, in this case of the filter cover paper is carried out (sic).

For this, there is a one-part or two-part sliding plate 1, over which the filter cover paper 10 runs in order to prevent a fluttering of the paper. This plate 1 can be a plate incorporated specifically into the machine, and it is also possible to use for this purpose the brush heating which is present on older machines and which was previously necessary when slow-drying glues were used.

The sliding plate preferably has a curvature with a radius of >50 cm, especially 80 cm.

Sensors 12 arranged in a row are inserted into recesses of the plate 1 transversely relative to the running direction of the filter cover paper. The filter cover paper thus runs over the sensors with its side not having the glue coating.

The sensors are capacitive sensors which, in their measuring region, react to changed moisture contents in their measuring region. The sensors can therefore detect and evaluate the moisture of the glue coating on the side located opposite the filter cover paper.

FIG. 2 shows a top view of a portion of a filter cover paper. The regions 16 to 21 forming the ventilation zones in the filter of the finished cigarette are excluded from the glue coating. A complete glue coating is necessary in the remaining regions, with the exception of the parting region 22. To detect this, on the side of the cover paper located opposite the glue there are the sensors 12 to 15 which each detect the glue coating of the filter cover paper in a narrow strip. The sensors 12 and 15 at the same time detect the outer regions of the filter cover paper which constitute the region provided for the connection of the filter to the cigarette. The sensors 13 and 14 detect the region of the filter cover paper in which the ventilation zones are provided. Between every two ventilation portions there is a glue coating which makes the edge connection when the filter cover paper is wound round the filter. A portion of the filter cover paper located between two transverse broken lines is provided for each cigarette.

FIG. 3 shows the mounting of the sensors. There are two holders 23 and 25 which hold the sliding plate 1 and which are displaceable in the axial direction of a shaft 27 by means of setscrews 24 and 26. The sensors 12 to 15 themselves are arranged displaceably in the axial direction in recesses of the holders 23 and 25 and can be fixed via setscrews 28 to 31. The sensors can thus be set exactly to the width and tracking of the filter cover paper. In a particular exemplary embodiment of the invention, the sensors are arranged somewhat below the surface of the holders. Dielectric material is inserted into the space thus formed between the sensors and surface, in order to prevent a soiling of the spaces. This arrangement makes it possible to increase the measuring reliability in the event of a possible fluttering of the filter cover paper.

FIG. 4 shows a top view of a one-part sliding plate. A plurality of individual channels (40–51) with a width of, for example, 1 mm and a depth of 2 mm are milled into the surface of the sliding plate 1 at an angle of approximately 45° relative to the running direction of the filter cover paper. The channels extend as far as the edges of the sliding plate, in order to allow a free inflow and outflow of air. The channels ensure that no air cushion which could cause the filter cover paper to flutter and therefore prevent a proper measurement forms between sliding plate and filter cover paper.

Additionally or alternatively, a suction source 52–59 can be connected to the channels, in order to generate a particular pressure force of the filter cover paper against the sliding plate.

Also, instead of a solid sliding plate, there can be a perforated grid plate through which the air can escape directly.

FIG. 5 shows a side view of a sliding plate. To prevent an air interspace between sliding plate and filter cover paper, here there is a sharp run-on edge 61, at which air adhering to the filter cover paper 10 is dissipated. This can be further assisted by suction via the suction channel 60.

FIG. 6 shows a block diagram of the evaluation circuit used in the invention. A capacitive sensor 12 detects the state of the glue coating on the filter cover paper running past, in that the dielectric in the measuring region of the sensor changes as a function of the moisture content of the glue coating.

The detected capacitance is converted via the converter 32 into a voltage $V_{LS}$ which is amplified via the amplifier 33 as a signal $V_L$. After the amplifier 33, the measured signal can be displayed, with the result that the "glue force" can be detected by measurement. A direct-voltage fraction is separated off in the comparator stage 34. The signals detected by the sensor are then converted into square-wave signals $V_F$. The $V_F$ signals are transmitted to a pulse stage which is triggered by the rising edge of the $V_F$ signal. The generated pulse $V_{FS}$ has a length of duration t which is matched to the running speed of the filter-attaching machine, for example 7,000 cigarettes per minute.

For the sensors located in the regions of the filter cover paper which have an uninterrupted tracking, the following applies: as soon as the glue coating is no longer sufficient or a gap occurs in the glue coating, the comparator 34 generates a voltage jump which, in the following pulse stage 35, generates a trigger signal $V_{FS}$ representing a fault signal. This can be displayed via an indicator 39 or can be transmitted as a control signal to the filter-attaching machine, in order for a specific time to eject the cigarettes produced out of the production cycle or to cut off the machine as a whole. The indicator 39 can also be connected directly via the switch 38 to the signal $V_F$ emitted by the comparator.

As regards the region of the filter cover paper which has the ventilation zones, the sensors generate a pulse train, from which a fault signal cannot be derived directly. Consequently, the square-wave signal generated in the pulse stage 35 has such a length that, whenever the glue coating is faultless, a new trigger pulse occurs before the end of the generated pulse and retriggers the pulse stage so that the generated pulse is constantly lengthened. Only when a trigger pulse is absent as a result of a defective glue coating does the pulse generated in the pulse state terminate, and therefore the failure of the pulse can be evaluated as a fault signal for controlling the filter-attaching machine.

The signal $V_F$ can also be used to synchronize the glue coating with the location of the cutting of the cover paper for the individual cigarettes. Thus, an exactly defined cutting point can be fixed on the cover paper.

The duration of the pulse generated in the pulse stage 35 can be put at a constant setting via a switch 37. Preferably, however, the length of the pulse is made dependent on the rotational speed of the filter-attaching machine, in that a control signal is transmitted via an amplifier 36 to the pulse stage 35 for determining the pulse length. The circuit therefore also works perfectly at different rotational speeds, especially also in the starting range of the machine.

List of reference symbols

1 Plate
2 Roller
3 Glue roller
4 Dipping roller
5 Pot
6 Glue
7 Sensor
8 Glue bead
9 Deflecting roller
10 Paper strip
11 Deflecting roller
12-15 Sensors
16-21 Ventilation region
22 Parting track
23 Holder
24 Setscrew
25 Holder
26 Setscrew
27 Shaft
28-31 Setscrew
32 Converter
33 Amplifier
34 Comparator
35 Pulse stage
36 Amplifier
37 Switch
38 Switch
39 Lamp
40-51 Channels
52-59 Suction connections
60 Suction channel
61 Run-on edge

We claim:

1. A device for detecting a sufficient glue coating on a first surface of a paper strip to be adhesively bonded in a cigarette machine, comprising:
    a sliding plate having a plate surface engaging a second surface of the paper strip, opposite to the first surface, and over which the paper strip runs in a first direction, said plate surface having groove-shaped channels oriented at angles of between 10 degrees and 80 degrees relative to said first direction;
    a plurality of capacitive sensors, for detecting presence of moisture in the glue coating on the first surface of the paper strip, directed toward the second surface of the paper strip, mounted in recesses in said plate surface of said sliding plate and arranged in a row extending transversely to said first direction; and
    a control means coupled to said sensors for evaluating signals emitted from said sensors and for emitting a fault signal for controlling the cigarette machine when the moisture sensed in the glue coating is insufficient.

2. A device according to claim 1 wherein said sliding plate is curved in said first direction with a radius of curvature greater than 50 centimeters.

3. A device according to claim 1 wherein said angles are about 45 degrees.

4. A device according to claim 1 wherein said sliding plate comprises a plurality of suction connections across a width of the paper strip.

5. A device according to claim 4 wherein said suction connections open into said groove-shaped channels in said plate surface of said sliding plate.

6. A device according to claim 1 wherein said sliding plate comprises a sharp run-on edge.

7. A device according to claim 1 wherein said sensors are arranged at a distance below said plate surface of said sliding plate; and wherein a dielectric material is introduced between said sensors and said plate surface of said sliding plate.

8. A device according to claim 1 wherein the paper strip is filter cover paper on which the glue coating is applied in a discontinuous, recurring pattern; and
    wherein said control means comprises a time frame with a specific segment duration which is predetermined, said fault signal being generated when a sufficient moisture content cannot be detected at an end of a time-frame segment.

9. A device according to claim 8 wherein the time-frame segments have lengths dependent on cigarette machine speed.

10. A cigarette forming machine, comprising:
    glue applicator means for applying a glue coating on a first surface a filter paper strip to be adhesively bonded about filters and cigarettes;
    a sliding plate having a plate surface engaging a second surface of the filter paper strip, opposite to the first surface, and over which the filter paper strip runs in a first direction, said plate surface having groove-shaped channels oriented at angles of between 10 degrees and 80 degrees relative to said first direction;
    a plurality of capacitive sensors, for detecting presence of moisture in the glue coating in a discontinuous, recurring pattern on the first surface of the filter paper strip, directed toward the second surface of the filter paper strip, mounted in recesses in said plate surface of said sliding plate and arranged in a row extending transversely to said first direction;
    a control means coupled to said sensors for evaluating signals emitted from said sensors and for emitting a fault signal for controlling the cigarette machine when the moisture sensed in the glue coating is insufficient; and
    conveying means for moving the filter paper strip to and from said glue applicator and said sliding plate.

11. A cigarette forming machine according to claim 10 wherein said sliding plate is curved in said first direction with a radius of curvature greater than 50 centimeters.

12. A cigarette forming machine according to claim 10 wherein said angles are about 45 degrees.

13. A cigarette forming machine according to claim 10 wherein said sliding plate comprises a plurality of suction connections across a width of the filter paper strip.

14. A cigarette forming machine according to claim 13 wherein said suction connections open into said groove-shaped channels in said plate surface of said sliding plate.

15. A cigarette forming machine according to claim 10 wherein said sliding plate comprises a sharp run-on edge.

16. A cigarette forming machine according to claim 10 wherein said sensors are arranged at a distance below said plate surface of said sliding plate; and wherein a dielectric material is introduced between said sensors and said plate surface of said sliding plate.

17. A cigarette forming machine according to claim 10 wherein said glue applicator means applies the glue coating in a discontinuous, recurring pattern; and
   wherein said control means comprises a time frame with a specific segment duration which is predetermined, said fault signal being generated when a sufficient moisture content cannot be detected at an end of a time-frame segment.

18. A cigarette forming machine according to claim 17 wherein the time-frame segments have lengths dependent on cigarette forming machine speed.

* * * * *